| United States Patent [19] | [11] 4,113,444 |
| Bunting et al. | [45] Sep. 12, 1978 |

[54] MICROBICIDE FOR USE WITH HYDROCARBON FUELS

[75] Inventors: Pamela M. Bunting, Cheswick; John F. Deffner, Glenshaw, both of Pa.

[73] Assignee: Gulf Research & Development Co., Pittsburgh, Pa.

[21] Appl. No.: 751,256

[22] Filed: Dec. 17, 1976

[51] Int. Cl.$^2$ .............................................. C10L 1/22
[52] U.S. Cl. .................................... 44/72; 424/349
[58] Field of Search ........................... 44/72; 424/349

[56] References Cited

U.S. PATENT DOCUMENTS

| 3,409,421 | 11/1968 | Belo et al. | 44/72 |
| 3,541,162 | 11/1970 | Larkin et al. | 44/72 |

*Primary Examiner*—Winston A. Douglas
*Assistant Examiner*—Y. Harris-Smith

[57] ABSTRACT

This invention relates to the inhibition of microbial growth in liquid distillate hydrocarbon fuels and more particularly to the use of halonitro alcohols as microbicides which effectively inhibit microbial growth in liquid distillate hydrocarbon fuels when incorporated therein at low concentrations.

13 Claims, No Drawings

MICROBICIDE FOR USE WITH HYDROCARBON FUELS

BACKGROUND OF INVENTION

1. Field of Invention

Liquid distillate hydrocarbon fuels, espeically those fuels which have minor concentrations of water entrained in the fuel composition, support a wide variety of gel-forming microorganisms which tend to deposit in the form of slime, sludge and other forms of precipitous undesirables and cause fuel storage tank corrosion, malfunctioning of distillate fuel oil burners, internal combustion engines (including gasoline and diesel engines), and jet turbine engines due to accumulations of gelatinous deposits in fuel tanks and lines, strainers, burner nozzles, filters, needle valves, level controls and the like. In numerous instances, physically removing the gelatinous deposits has failed to solve the problem of additional accumulations of the gelatinous deposits.

It has now been discovered that a small but effective amount of a halonitro alcohol added to a binary liquid distillate hydrocarbon fuel system containing an aqueous phase, alleviates the problem of gel-formation by killing and inhibiting the growth of microorganisms which produce the gel.

2. The Prior Art

The problem of gel-formation in hydrocarbon fuel systems is known and several attempts have been made in the past to solve the problem. For example, U.S. Pat. No. 3,259,478, issued to Thayer, on July 5, 1966 for Bacteria-Inhibited Fuel Composition, relates to growth inhibition of slime promoting microorganisms in the presence of hydrocarbon distillate fuels containing entrained water. In particular, microorganism growth in fuel systems containing water is said to be inhibited by incorporating in the fuel a small amount of a microbicide selected from the group of 2-nitroresorcinol, 4-nitroresorcinol, 4-nitrosoresorcinol and nitrocatechol. The antimicrobial agents are primarily described as oil soluble, with the capability of partition between the two phases in a fuel-water binary system.

The use of 2-bromo-2-nitropropane-1, 3-diol to suppress bacterial growth is described in U.S. Pat. No. 3,707,148 issued to Bryce on Dec. 26, 1972, for Impregnated Diaper, which teaches the incorporation of 2-bromo-2-nitropropane-1, 3-diol and a monomeric acid, such as citric acid, in a substrate, for example, a diaper, to absorb ammonia and inhibit the growth of ammonia-producing bacteria to prevent diaper rash associated with infants.

U.S. Pat. No. 3,024,192, issued to Bennett et al, on Mar. 6, 1962, entitled "Process for the Control of Bacteria in a Flooding Process for the Recovery of Petroleum Oil", teaches the use of halonitroalkanols to control sulfur-reducting bacteria, such as *Desulfovibrio desulfuricans*, in the secondary recovery of petroleum oils. This is accomplished by incorporating into the flooding water effective amounts of halonitroalkanols.

Another use for 2-bromo-2-nitropropane-1, 3-diol is disclosed in U.S. Pat. No. 3,907,539 issued to Holdt et al, on Sept. 23, 1975 for a Process for Preserving Cut Flowers. In particular, the reference discloses an aqueous nutrient concentrate composition which is described as suitable for preserving cut flowers. The aqueous concentrate comprises sugar, an acid-reacting substance(s), 2-bromo-2-nitropropanediol-(1,3) and a plant growth promoting compound(s). The 2-bromo-2-nitropropanediol-(1,3) is utilized in the context of a germicidal agent.

Canadian Pat. No. 742,668, issued to Kline et al, on Sept. 13, 1966, entitled "Antimicrobial Compositions and Process", relates to the use of antimicrobial and antifungal agents to suppress the growth of microorganisms in hydrocarbon fuels. In particular, the reference teaches the use of nitrosubstituted benzonitriles as antibacterial and antifungal agents.

SUMMARY OF INVENTION

This invention relates to a process for inhibiting the growth of gel-forming microorganisms in a binary liquid system comprising a major amount of a liquid distillate hydrocarbon fuel oil and a minor amount of an aqueous phase, at least one of said liquid distillate hydrocarbon fuel oil and said aqueous phase being contaminated with gel-deposit forming microorganisms, by adding to said binary liquid system a microbicidal amount of a halonitro alcohol of the formula:

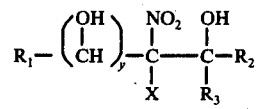

wherein $R_1$, $R_2$ and $R_3$ are either alike or different members selected from hydrogen or alkyl having from 1 to about 7 carbon atoms; and Y is an integer selected from 0 or 1; and X is selected from bromine, chlorine or iodine.

DETAILED DESCRIPTION OF INVENTION

It has now been recognized that gel-forming microorganisms grow in liquid distillate hydrocarbon fuels, especially those fuels which contain small amounts of entrained water. These microorganisms tend to emulsify hydrocarbon fuel and water forming slimes or gels, which contain the microorganisms, both living and dead, their by-products, rust particles, and other minute debris in suspension. These gels cause storage tank corrosion and equipment failure due to accumulation of gelatinous deposits in fuel lines, strainers, burner nozzles, filters, needle valves and the like.

Many microorganisms can and do flourish in binary-phase liquid distillate hydrocarbon fuels containing entrained moisture in the form of water bottoms. In the absence of entrained water in the liquid distillate hydrocarbon fuel system, no significant microbial growths are noted, however, the microorganisms are capable of surviving in a dormant or spore stage for long periods of time and are present to contaminate the fuel upon introduction of water into the system.

A wide variety of microorganisms, including aerobic and anaerobic bacteria, fungi and yeasts have been found to exist in liquid distillate hydrocarbon fuel storage tanks, among the more commonly isolated microorganisms are bacteria such as Pseudomonas, Bacillus, Flavobacterium, Micrococcus, Desulfovibrio; fungi such as Cladosporium, Hormodendrum, Aspergillus, Penicillium; and common yeasts such as Candida and Torula. These microorganisms appear to require water for life and thrive at the hydrocarbon fuel-water interface, but a few are capable of existing in the hydrocarbon phase as well.

Water enters the hydrocarbon fuel system via a variety of sources and either already contains nutrient mineral salts which promote microbial growth or is a good solvent for them. For example, at the refinery, gasoline and kerosene type fuels are often washed with river water. Most of the water readily separates from the fuel due to difference in density and the action of gravity. However, small amounts of water remain entrained in the hydrocarbon fuel and are transported to storage tanks with the fuel.

It is not considered likely that the hydrocarbon fuel is contaminated prior to distillation, since the high temperatures and steam stripping to which the fuel is subjected during distillation would tend to disinfect the fuel. On the other hand, it has been discovered that the water used in the conventional waterwashing of distillate fuels that have been previously treated with aqueous treating reagents, for example, aqueous caustic soda (sodium hydroxide) solution, as well as the water used in preparing the aqueous treating reagents, themselves, can contain microorganisms of the kind found in fuel oil gels and/or spores thereof. It should be noted that water which contains an extremely minute concentration of living gel-forming microorganisms or spores can constitute a very effective source of infection of distillate hydrocarbon fuels. In some storage facilities, particularly those containing light hydrocarbon fuels and products, water is purposely introduced into storage tanks to prevent loss of the fuels and products due to seepage at the bottom of the tanks. Water is additionally introduced into storage facilities due to "breathing" of the tanks. Breathing in a storage tank occurs when a temperature change in the tank causes a change in the tank's vapor pressure. An increase in temperature causes the vapor pressure to increase while a decrease in temperature causes the storage tank vapor pressure to decrease and draw air into the tank. Thus, breathing results in the introduction of atmospheric water into the storage tank due to condensation of moisture in air. It is obvious from the above statements, that contamination of distillate hydrocarbon fuels by water and hydrocarbon fuel assimilating microbes is common and exceedingly difficult, if not practically impossible, to prevent or eliminate. Because of the large variety of microorganisms capable of existing in hydrocarbon fuel systems and the difficulty in identifying them, the microorganisms will be collectively referred to herein as hydrocarbon fuel-assimillating microbes. The binary liquid distillate hydrocarbon fuels being treated herein contain about 0.01 to about 99.0 weight percent water, generally about 0.1 to about 5.0 weight percent water, based on the liquid distillate hydrocarbon fuel.

The effect of microorganisms on stored liquid distillate fuels was not widely felt until the advent of jet-aircraft fuels and heating fuels which have a kerosene base. Paraffinic hydrocarbons having higher molecular weights, such as kerosene (about $C_{10}$ to about $C_{18}$), support more different types of microorganisms than lower molecular weight paraffinic hydrocarbons, such as gasoline (about $C_4$ to about $C_{12}$). Additionally, kerosene fuels are consumed at very high rates by jet engines and a small amount of microbial sludge in the fuel becomes a potential hazard which can rapidly clog fuel strainers.

The gels with which this invention is concerned have been found to occur primarily in the form of beads and films. Occasionally, however, the gel deposits are in fibrous form. When in relatively pure form the gels have been found to be clear and generally yellowish in color, but these characteristics are sometimes masked by contamination of the gel with black fuel oil sludge or other minute particles of debris normally present in hydrocarbon fuel systems.

It is now generally recognized by the petroleum industry that certain microorganisms utilize liquid distillate hydrocarbon fuels as a source of carbon and energy. Petroleum microbiologists have isolated hundreds of species capable of modifying solid, liquid and gaseous hydrocarbons. The harmful effects of these microorganisms in refined liquid distillate hydrocarbon fuels are now considered and recognized as a world-wide problem. These microorganisms derive their energy from the oxidation of hydrocarbons and utilize the hydrocarbon as cellular material. The by-products of microbial activity in such a system include growth accumulations, cellular debris, organic acids, carbon dioxide, rust particles, and the like. As the microbial growth proceeds, it often takes the appearance of brown-black mats, with a slime-like or stringy character. Microbial by-products additionally endanger storage tank integrity by damaging corrosion barriers, top-coatings and sealants employed in the tank.

It has now been discovered that microbial growth in binary liquid systems comprising a liquid distillate hydrocarbon phase and an aqueous phase, can be inhibited by adding a small but effective amount of a microbicidal agent selected from certain halonitro alcohols defined herein below. Specific examples of halonitro alcohols which are suitable for use in the present process include:

2-bromo-2-nitro-1-butanol;
1-bromo-1-nitro-2-pentanol;
2-bromo-2-nitropropane-1,3-diol;
1-bromo-1-nitro-2-hexanol;
1-bromo-1-nitro-3-methyl-2-butanol;
2-bromo-2-nitro-1-propanol;
3-bromo-3-nitro-4-methyl-2-pentanol;
3-bromo-3-nitro-2-methyl-pentane-2,4-diol;
4-bromo-2,6-dimethyl-4-nitroheptane-3,5-diol;
2-chloro-2-nitro-1-butanol;
1-chloro-1-nitro-2-pentanol;
2-chloro-2-nitropropane-1,3-diol;
1-chloro-1-nitro-2-hexanol;
1-chloro-1-nitro-3-methyl-2-butanol;
2-chloro-2-nitro-1-propanol;
3-chloro-3-nitro-4-methyl-2-pentanol;
3-chloro-3-nitro-2-methyl-pentane-2,4-diol;
2-iodo-2-nitro-1-butanol;
1-iodo-1-nitro-2-pentanol;
2-iodo-2-nitropropane-1,3-diol;
1-iodo-1-nitro-2-hexanol;
1-iodo-1-nitro-3-methyl-2-butanol;
2-iodo-2-nitro-1-propanol;
3-iodo-3-nitro-4-methyl-2-pentanol;
3-iodo-3-nitro-2-methyl-pentane-2,4-diol;
and mixtures thereof.

Normally, the halonitro alcohol is incorporated in the binary liquid system at a concentration of at least 1 part per million (ppm) of the aqueous phase, but generally below about 500 ppm, with a preferred range of from about 5 ppm to about 50 ppm of the aqueous phase. It should be noted that the halonitro alcohols used herein are substantially water soluble and substantially insoluble in liquid distillate hydrocarbon fuels.

The microbicides described herein can be added to the liquid distillate hydrocarbon fuel systems in any conventional manner. For example the microbicides can be added to fuel storage tanks as a solid which sinks through the fuel layer and dissolves in the water layer on the bottom. Alternatively, the microbicide can be added to the fuel storage system as a solid in a porous container which would allow water to enter the container, dissolve the microbicide and decontaminate the hydrocarbon fuel aqueous inter-face or as a water/microbicide mixture.

The present invention will normally find use after fuel tanks have been cleaned, although it can also be used with somewhat reduced effectiveness when storage tanks contain fuel that is infected with substantial proportions of gel-forming microorganisms. When used following cleaning of fuel storage tanks, the present invention will effectively prevent infection of the distillate fuel system. When applied to tanks containing a substantial amount of microbial sludges and gels, the present invention will disinfect the tank contents and thereby prevent the accumulation of additional sludge or gel. The microbicides disclosed herein can be incorporated in the distillate hydrocarbon fuel systems before or after contact with a source of microbial contamination, and they can be employed either alone or admixed with compatible diluents, solvents or blending agents that do not materially impair the microbicidal action of the agents.

Fuels that can be treated according to this invention are those hydrocarbon distillate fuels that tend to deposit gels due to the presence of gel-forming microorganisms. Specific examples of hydrocarbon distillate fuels include gasoline, aviation fuel, diesel fuels, No. 1 fuel oil, No. 2 fuel oil, and synthetic liquid hydrocarbon fuels produced from solid carbonaceous compounds.

Gasoline, as defined herein, is a blend of petroleum hydrocarbons boiling within the range of from about 80° F. (27° C.) to about 437° F. (225° C.), which occur naturally in petroleum and natural gas or are produced in various refining processes such as alkylation, catalytic cracking, thermal cracking, and reforming. Gasoline has a hydrocarbon range of from about $C_4$ to about $C_{12}$ and is defined in ASTM Designation: D-439-75.

Aviation fuels suitable for use herein, are kerosene type hydrocarbons boiling within the range of about 325° F. (163° C.) to about 572° F. (300° C.). These hydrocarbons contain from about 10 to about 18 carbon atoms and are defined in ASTM Designation: D-1655-75.

Diesel fuels suitable for use are petroleum hydrocarbons boiling within the range of from about 300° F. (149° C.) to about 680° F. (360° C.) and are set forth and defined with particularity in ASTM Designation: D-975-74.

No. 1 and No. 2 fuel oils are defined as petroleum hydrocarbons boiling within the range from about 320° F. (160° C.) to about 680° F. (360° C.) with 550° F. (288° C.) being the end point for No. 1 fuel oil and 340° F. (171° C.) being the minimum boiling point for No. 2 fuel oil. The definition for No. 1 and No. 2 fuel oil is set forth in greater detail in ASTM Designation: D-396-75.

Synthetic fuels suitable for use in the present process are derived from solid carbonaceous products conveniently prepared by blending finely ground carbonaceous material with a solvent to form a slurry. The slurry is then introduced into a reaction vessel containing a conventional hydrogenation catalyst and is reacted under normal hydrogenating pressures and temperatures. After hydrogenation, solids that are present can conveniently be removed from the product stream, for example, by filtration. The product is next stripped of solvent. The balance of the product stream may be distilled to obtain products of various boiling ranges. Some of the products are useful as fuels, the remainder can be further treated by a conventional petroleum process including cracking, hydrocracking, and the like.

Synthetic liquid fuels produced from solid carbonaceous products such as coal are primarily aromatic and generally have a boiling range of about 300° F. (149° C.) to about 1400° F. (760° C.), a density of about 0.9 to about 1.1 and a carbon to hydrogen molecular ratio in the range of about 1.3:1 to about 0.66:1. A typical example is a fuel oil obtained from a subbituminous coal, such as Wyoming-Montana coal or a bituminous coal, such as Pittsburgh seam coal; comprising a middle oil having a boiling range of from about 375° F. (190.5° C.) to about 675° F. (357° C.). A description of how to prepare a synthetic fuel from carbonaceous material is set forth in greater detail in U.S. Pat. No. 3,957,619 issued to Chun et al on May 18, 1976, entitled "Process for the Conversion of Carbonaceous Materials", the disclosure of which is incorporated herein by reference.

The microbicidal process of the present invention is further illustrated by the following examples, which should be construed as preferred embodiments to enable an artison to practice the invention.

EXAMPLES I TO VI

Two laboratory cultures of liquid distillate hydrocarbon fuel-assimilating microbes were prepared to determine the microbicidal activity of halonitro alcohols under laboratory conditions. The microorganisms were isolated from a biological waste treatment system at a petroleum refinery. Although not specifically identified, the microorganisms exhibited bacteria characteristics typical of the Pseudomonas genus. The test cultures were designated CS-299-4 and CS-300-6A.

The microorganisms were cultured in a Bushnell-Haas mineral salts medium comprising 1.0 gm of ammonium nitrate, 1.0 gm of dipotassium phosphate, 1.0 gm of monopotassium phosphate, 0.02 gm of calcium chloride, 0.2 gm of magnesium sulfate and 0.05 gm of ferric chloride, which was diluted with 1 liter of water and adjusted to ph 7.0. The microorganism contaminated Bushnell-Haas mineral salts medium was dispensed in 250 ml Erlenmeyer flasks in 100 ml amounts and 3.0 ml of gasoline were added as the carbon source.

Test samples containing cultures of the microorganisms and varying concentrations of 2-bromo-2-nitropropane-1,3-diol (e.g. 10 ppm to 50 ppm) were placed on a Model G-26 New Brunswick, rotary action shaker at 30° C. for 96 hours. The results are summarized in Table I below.

Table I

| | Shake Flask Experiments with 2-bromo-2-nitropropane-1,3-diol | | | Bacteria Count Bacteria per Milliliter | |
|---|---|---|---|---|---|
| Example | Treatment | Concentration (PPM) | Organism | Initial | 96 hours |
| I | Control | — | CS-299-4[1] | $1.5 \times 10^6$ | $3.5 \times 10^8$ |
| II | Control | — | CS-300-6A[2] | $3.3 \times 10^6$ | $1.0 \times 10^8$ |
| III | 2-bromo-2-nitropropane-1,3 diol[3] | 50 | CS-299-4 | $1.5 \times 10^6$ | <1 |

Table I-continued

Shake Flask Experiments with 2-bromo-2-nitropropane-1,3-diol

| Example | Treatment | Concentration (PPM) | Organism | Bacteria Count Bacteria per Milliliter | |
|---|---|---|---|---|---|
| | | | | Initial | 96 hours |
| IV | 2-bromo-2-nitropropane-1,3 diol[3] | 50 | CS-300-6A | $3.3 \times 10^6$ | <1 |
| V | 2-bromo-2-nitropropane-1,3 diol[3] | 25 | CS-299-4 | $7 \times 10^6$ | <1 |
| VI | 2-bromo-2-nitropropane-1,3 diol[3] | 10 | CS-299-4 | $7 \times 10^6$ | <1 |

[1] CS-299-4 = hydrocarbon fuel-assimilating bacterium,
[2] CS-300-6A = hydrocarbon fuel-assimilating bacterium
[3] The halonitro alcohols described in the specificaton herein can be substituted for the 2-bromo-2-nitropropane-1,3 diol with substantially the same results.

EXAMPLES VII TO XI

The procedure of Example I was followed with the following exceptions. Contaminated water bottoms from gasoline storage tanks which contained a variety of microorganisms provided the inoculum for the Bushnell-Haas mineral salts medium. 2-bromo-2-nitropropane-1, 3-diol rapidly killed the majority of the microbes when added to the aqueous phase of the gasoline/mineral salts medium cultures at concentrations of 5 ppm and 10 ppm. The few surviving cells did not significantly multiply during the fourteen day incubation period. The other halonitro alcohols described herein can be substituted for the 2-bromo-2-nitropropane-1, 3-diol above with substantially the same results. The above experiments are summarized in Table II below.

Table II

Effect of 2-bromo-2-nitropropane-1 3-diol on Viability of Gasoline-Assimilating Microorganisms

| Example | Inoculum | Treatment | Concentration of 2-bromo-2-nitropropane-1 3-diol (PPM) | Initial | 1 day | 3 days | 9 days | 14 days |
|---|---|---|---|---|---|---|---|---|
| VII | Contaminated gasoline tank Water bottoms | Control | — | $1.6 \times 10^4$ | $10^3$ | $10^6$ | $10^8$ | $2.0 \times 10^8$ |
| VIII | Contaminated gasoline tank Water bottoms | 2-bromo-2-nitropropane-1,3-diol | 10 | $1.6 \times 10^4$ | 2 | 6 | 5 | 4 |
| IX | Contaminated gasoline tank Water bottoms | 2-bromo-2-nitropropane-1,3-diol | 5 | $1.6 \times 10^4$ | 4 | 5 | 7 | 4 |
| X | Mixed Culture CS-299-4; CS-300-6A | Control | — | $2.2 \times 10^6$ | $1.4 \times 10^7$ | $6.0 \times 10^8$ | $6.0 \times 10^8$ | $6.0 \times 10^8$ |
| XI | Mixed Culture CS-299-4; CS-300-6A | 2-bromo-2-nitropropane-1,3-diol | 10 | $2.2 \times 10^6$ | 0 | 0 | 0 | 0 |

EXAMPLES XII TO XV

The procedure of Example I was followed with the following exception. Microorganisms were isolated from No. 2 fuel-oil water bottoms and used to inoculate a Bushnell-Hass mineral salts medium dispensed in 100 ml amounts in 250 ml Erlenmeyer flasks containing 3.0 ml of No. 2 fuel-oil as the carbon source. Duplicate flasks were prepared containing 0 ppm, 5 ppm, 10 ppm and 25 ppm of 2-bromo-2-nitropropane-1,3-diol.

The inoculated flasks were placed on a rotary shaker at 30° C. for incubation. At intervals of 1,5,7,12 and 16 days, a 1.0 ml aliquot was removed from each flask, diluted and plated to determine the number of surviving microorganisms.

Table III below summarizes observations and conclusions of the experiments.

Table III

Effect of 2-bromo-2-nitropropane-1,3-diol on the Survival & Growth of Microorganisms Cultured From Heating Oil Water Bottoms

| | | Microorganisms Count (cells/ml) | | | |
|---|---|---|---|---|---|
| Example Time of Incubation | XII Control | XIII 5 ppm Bronopol | XIV 10 pp Bronopol | XV 25 ppm Bronopol | |
| 0 day | $6 \times 10^4$/ml | $6 \times 10^4$/ml | $6 \times 10^4$/ml | $6 \times 10^4$/ml | |
| 1 day | $3 \times 10^6$/ml | $1.0 \times 10^3$/ml | $1.5 \times 10^3$/ml | $2.0 \times 10^3$/ml | |
| 5 days | $5 \times 10^8$/ml | $2.0 \times 10^3$/ml | $3.0 \times 10^3$/ml | $1.5 \times 10^3$/ml | |
| 7 days | $2 \times 10^8$/ml | $3.0 \times 10^3$/ml | $1.5 \times 10^3$/ml | $1.0 \times 10^3$/ml | |
| 12 days | $1 \times 10^8$/ml | $4.0 \times 10^3$/ml | $2.5 \times 10^3$/ml | $5.0 \times 10^3$/ml | |
| 16 days | $3 \times 10^7$/ml | $1.5 \times 10^3$/ml | $2.0 \times 10^3$/ml | $1.0 \times 10^3$/ml | |

The above table indicates that 2-bromo-2-nitropropane-1,3-diol added to water bottoms of fuel-oil storage tanks at concentrations of 5 ppm or higher effectively eliminates the majority of microorganisms present and prevents the growth of any that survive. Substantially the same results are obtained when the remaining halonitro alcohols described herein are substituted for the 2-bromo-2-nitropropane-1,3-diol above.

Obviously, many modifications to the above examples can be made with similar results. In particular when the halonitro alcohols defined herein are added to the water bottoms of diesel fuels and aviation fuels not included in the specific examples, substantially the same results are obtained.

What is claimed is:

1. A process for inhibiting the growth of gel-forming micro-organisms in a binary liquid system comprising a major amount of a liquid distillate hydrocarbon fuel and a minor amount of an aqueous phase, which comprises adding to said binary liquid system a microbicidal amount of a water soluble halonitro alcohol of the formula:

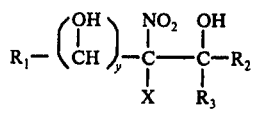

wherein $R_1$, $R_2$ and $R_3$ are either alike or different members selected from hydrogen or alkyl having from 1 to about 7 carbon atoms; and Y is an integer selected from 0 or 1; and X is selected from bromine, chlorine or iodine.

2. The process according to claim 1 wherein said liquid distillate hydrocarbon fuel is gasoline.

3. The process of claim 1 wherein the liquid distillate hydrocarbon fuel is No. 1 heating oil.

4. The process according to claim 1 wherein said liquid distillate hydrocarbon fuel is No. 2 heating oil.

5. The process of claim 1 wherein the liquid distillate hydrocarbon fuel is diesel fuel.

6. The process according to claim 1 wherein said liquid distillate hydrocarbon fuel is aviation fuel.

7. The process of claim 1 wherein the liquid distillate hydrocarbon fuel is a synthetic liquid fuel derived from solid carbonaceous compositions.

8. The process according to claim 1 wherein the halonitro alcohol is selected from the group of:

2-bromo-2-nitro-1-butanol;
1-bromo-1-nitro-2-pentanol;
2-bromo-2-nitropropane-1,3-diol;
1-bromo-1-nitro-2-hexanol;
1-bromo-1-nitro-3-methyl-2-butanol;
2-bromo-2-nitro-1-propanol;
3-bromo-3-nitro-4-methyl-2-pentanol;
3-bromo-3-nitro-2-methyl-pentane-2,4-diol;
4-bromo-2,6-dimethyl-4-nitroheptane-3,5-diol;
2-chloro-2-nitro-1-butanol;
1-chloro-1-nitro-2-pentanol
2-chloro-2-nitropropane-1,3-diol;
1-chloro-1-nitro-2-hexanol;
1-chloro-1-nitro-3-methyl-2-butanol;
2-chloro-2-nitro-1-propanol;
3-chloro-3-nitro-4-methyl-2-pentanol;
3-chloro-3-nitro-2-methyl-pentane-2,4-diol;
2-iodo-2-nitro-1-butanol;
1-iodo-1-nitro-2-pentanol;
2-iodo-2-nitropropane-1,3-diol;
1-iodo-1-nitro-2-hexanol;
1-iodo-1-nitro-3-methyl-2-butanol;
2-iodo-2-nitro-1-propanol;
3-iodo-3-nitro-4-methyl-2-pentanol; or
3-iodo-3-nitro-2-methyl-pentane-2,4-diol;
and mixtures thereof.

9. The process of claim 1 wherein said halonitro alcohol is 2-bromo-2-nitropropane-1,3-diol.

10. The process according to claim 1 wherein the aqueous phase comprises from about 0.01 to about 99 weight percent of the binary liquid system.

11. The process of claim 1 wherein the aqueous phase comprises from about 0.1 to about 5.0 weight percent of the binary liquid system.

12. The process of claim 1 wherein the microbicidal amount of the halonitro alcohol comprises from about 1 ppm to about 500 ppm of the aqueous phase.

13. The process according to claim 1 wherein the microbicidal amount of the halonitro alcohol comprises from about 5 ppm to about 50 ppm of the aqueous phase.

* * * * *